United States Patent
White

(10) Patent No.: US 6,263,748 B1
(45) Date of Patent: Jul. 24, 2001

(54) MECHANICAL METHOD FOR CHANGING OXYGEN SENSOR CHARACTERISTICS

(75) Inventor: Vincent Arthur White, Northville, MI (US)

(73) Assignee: General Motors Corporation, Detroit, MI (US)

(*) Notice: Subject to any disclaimer, the term of this patent is extended or adjusted under 35 U.S.C. 154(b) by 0 days.

(21) Appl. No.: 09/413,699

(22) Filed: Oct. 6, 1999

(51) Int. Cl.[7] ................................................. G01D 21/00
(52) U.S. Cl. ................................... 73/866.5; 204/408
(58) Field of Search ............... 73/23.32, 118.1, 73/866.5; 204/408

(56) References Cited

U.S. PATENT DOCUMENTS

| | | | |
|---|---|---|---|
| 3,844,920 | * 10/1974 | Burgett et al. | 204/195 S |
| 3,847,778 | * 11/1974 | Riddel | 204/195 S |
| 4,038,034 | * 7/1977 | Nakajima et al. | 23/255 E |
| 4,040,930 | * 8/1977 | Dillon | 204/195 S |
| 4,049,524 | * 9/1977 | Togawa et al. | 204/195 S |
| 4,096,050 | * 6/1978 | Kobayashi et al. | 204/195 S |
| 4,184,934 | * 1/1980 | Bobe et al. | 204/195 S |
| 4,198,279 | * 4/1980 | Brown et al. | 204/195 S |
| 4,407,704 | * 10/1983 | Mase et al. | 204/1 T |
| 5,137,616 | * 8/1992 | Poor et al. | 204/428 |

* cited by examiner

Primary Examiner—Hezron Williams
Assistant Examiner—C D Garber
(74) Attorney, Agent, or Firm—Anthony Luke Simon

(57) ABSTRACT

A method for determining the mechanical installation parameters of an oxygen sensor so that it will operate within a predetermined temperature range under all operating conditions of the vehicle by setting the desired exposed area of the sensor element tip (S), taking into account: the recommended maximum operational temperature of the oxygen sensor ($T_s$); the hottest expected temperature of the exhaust gas ($T_g$); the effective heat transfer rate from the exhaust gas to the sensor element tip, and ultimately to the surroundings, ie., the exhaust pipe sidewall which is in contact with the surrounding ambient air (Q/t); the thermal conductivity of the oxygen sensor (k); and an effective thickness, which depends on where the temperature is measured in the oxygen sensor (x), according to a relation: $S=(Q*x)/((T_g-T_s)(t*c*k))$. The exposed surface area is then mechanically set, which may include use of a collar concentrically placed around the sensor element tip.

11 Claims, 2 Drawing Sheets

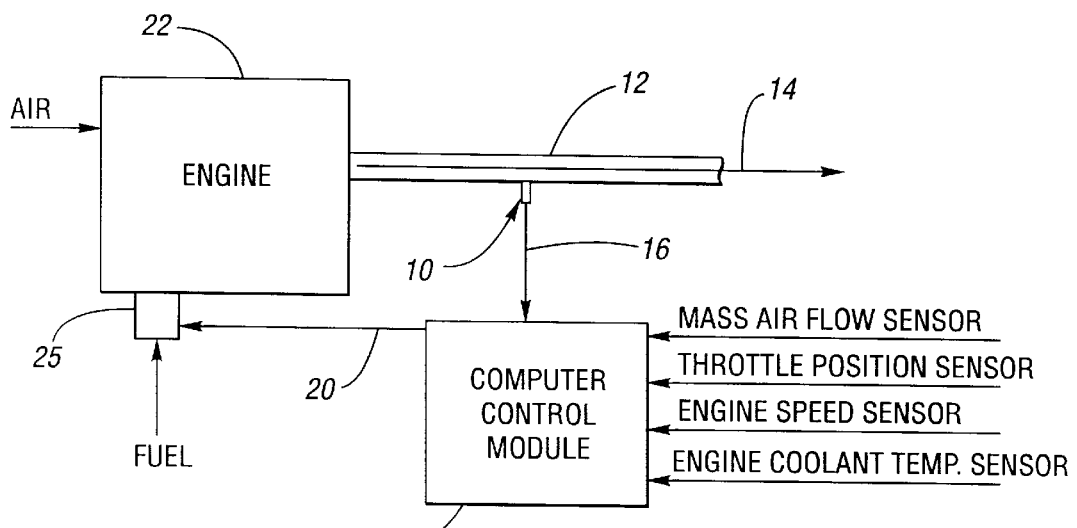
*Prior Art*
*Fig. 1*
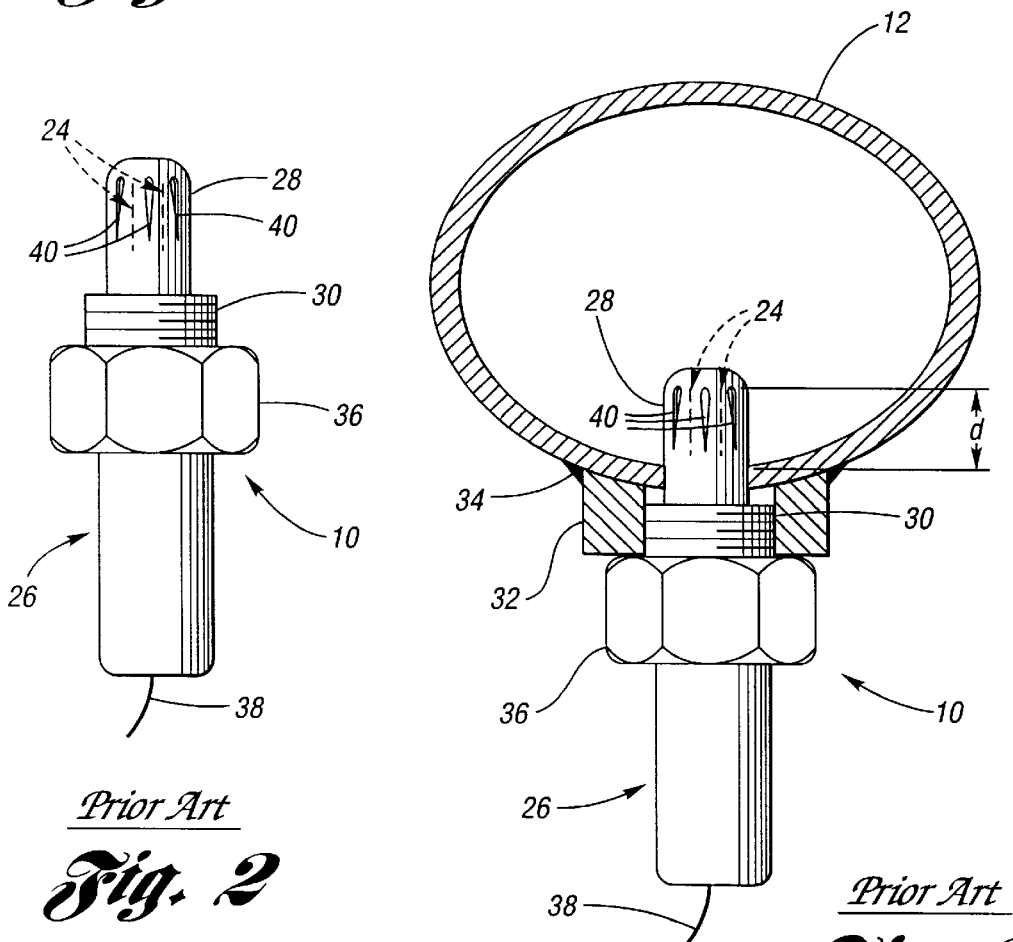
*Prior Art*
*Fig. 2*
*Prior Art*
*Fig. 3*

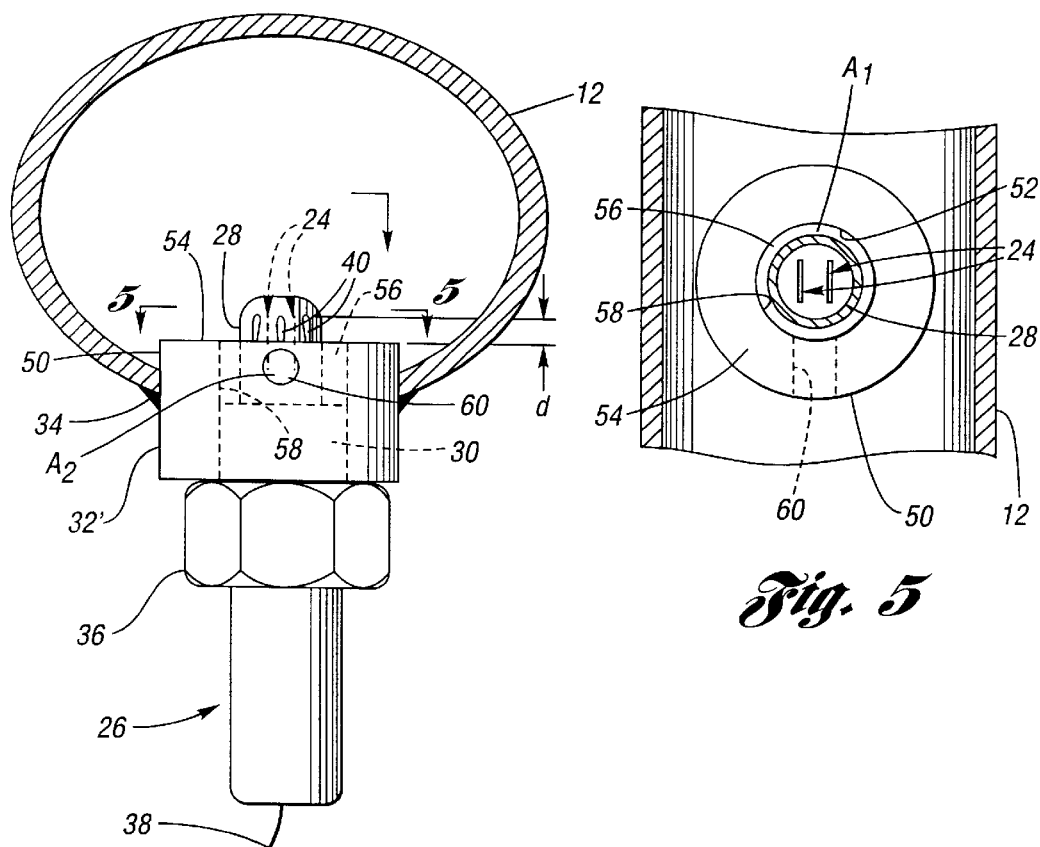
Fig. 4
Fig. 5
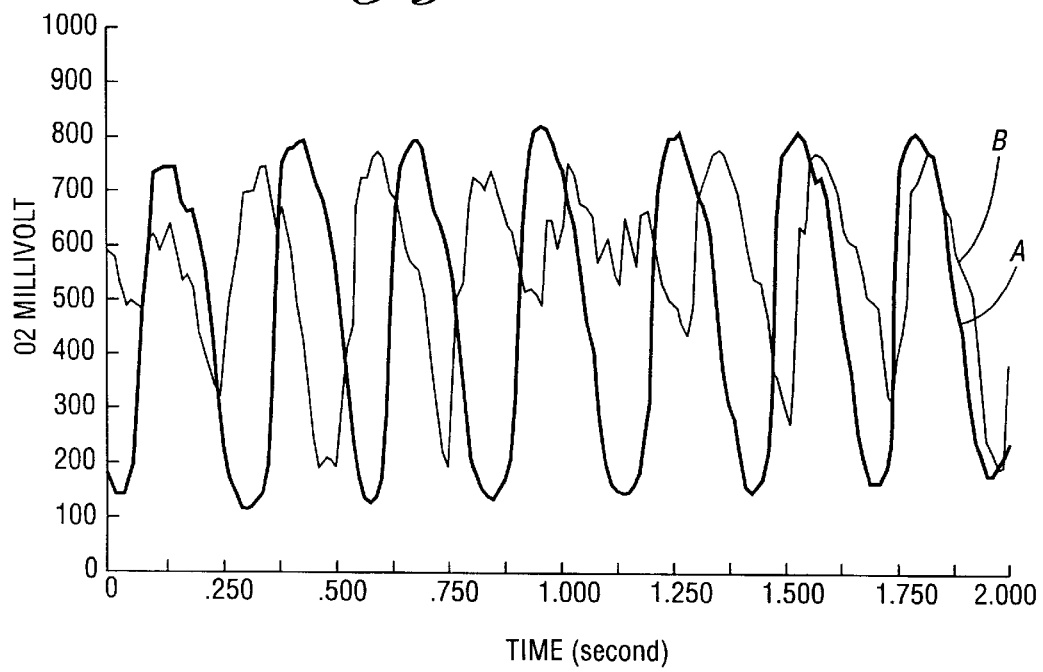
Fig. 6

MECHANICAL METHOD FOR CHANGING OXYGEN SENSOR CHARACTERISTICS

BACKGROUND OF THE INVENTION

1. Field of the Invention

The present invention relates to oxygen sensors used in association with the internal combustion engine of motor vehicles, and more particularly for a method of adjustment thereto.

2. Description of the Prior Art

Oxygen sensors are used in virtually all currently produced gasoline internal combustion engines used for vehicles operated in the United States. As shown diagrammatically at FIG. 1, the oxygen sensor 10 is located at exhaust pipe 12 so as to be in communication with the exhaust gas 14 therein in order to sense the oxygen content thereof, and provide an output signal voltage 16 responsive thereto. This oxygen sensor output signal voltage 16 is input, along with other sensor signals, to the engine computer control module (CCM) 18, which then, based upon predetermined criteria, provides one or more signals 20 to various components associated with the engine 22, particularly the fuel injector 25, to optimally adjust operational parameters thereof to provide performance yet minimize both fuel consumption and exhaust gas pollution.

As shown at FIGS. 2 and 3, the oxygen sensor 10 is a device consisting of a zirconia ceramic sensor element tip 24 for producing the output signal voltage 16 (see FIG. 1), wherein the sensor element tip is mounted to a housing 26 and protected by a perforated cover 28, whereby the perforations 40 allow the exhaust gas to contact the sensing element tip. The oxygen sensor 10 has threads 30 for being threadably mounted to a mounting member 32 via a hex 36. The mounting member 32 is, in turn, welded 34 to the exhaust pipe 12. The housing 26 and the weld 34 prevent exhaust gas from escaping the exhaust pipe 12 thereat. An output signal wire 38 is connected to the sensor element tip 24, emanates from the housing 26, and is connected (typically) to the engine CCM 18 (see FIG. 1).

The technique to locate an oxygen sensor in the exhaust pipe has not changed over the last twenty-five years: the housing 26 of the oxygen sensor 10 is screwed into the mounting member 32, whereby the sensing element tip 24 extends outwardly a distance d equal to about fifteen millimeters. This technique while simple and repeatable, is not always optimal. The reason for this is that for the oxygen sensor is most accurate when operated within a specific temperature range set by the manufacturer. While heaters may provide a temperature at or above a low-side value of the specific temperature range for the oxygen sensor when the exhaust gas is cold (i.e., a cold engine start), there is no reasonable way to cool the temperature of the oxygen sensor to an allowable high-side value of the specific temperature range when the temperature of the exhaust gas exceeds this value. This later case may occur, for example, when the vehicle is towing and traveling upgrade, and heavy trucks are most prone to experiencing this behavior.

One way to limit higher end operational temperature of the oxygen sensor may be to place the oxygen sensor further downstream along the exhaust pipe. But, in practice, the excessive distance needed for a noticeable drop in exhaust gas temperature (as for example fifteen feet) renders this an impractical solution. Another solution may be to make the outward extension distance d smaller, on the theory that the reduced contact surface area will result in less heat exchanged with the exhaust gasses and the heat transfer rate away from the sensor element tip will be the same or improved (because of the shortened heat conduction path to the exhaust pipe sidewall). However, in practice the extension distance d may become too small, such that insufficient exposure to the exhaust gas can occur, resulting in less accurate output signal voltages.

Accordingly, what remains needed in the art is some method whereby the oxygen sensor may be installed and operate within the temperature limits set by the manufacturer under all operating conditions of the vehicle.

SUMMARY OF THE INVENTION

The present invention is a method for determining the mechanical installation parameters of an oxygen sensor so that it will operate within the temperature limits set by the manufacturer under all operating conditions of the vehicle.

The method according to the present invention sets the appropriate exposed area of the sensor element tip (S), calculated from a formula which takes into account: the recommended maximum operational temperature of the oxygen sensor ($T_s$); the hottest expected temperature of the exhaust gas ($T_g$); the effective heat transfer rate from the exhaust gas to the sensor element tip, and ultimately to the surroundings, i.e., the exhaust pipe sidewall which is in contact with the surrounding ambient air (Q/t); the thermal conductivity of the oxygen sensor (k); and an effective thickness, which depends on where the temperature is measured in the oxygen sensor (x).

This calculation is represented by equation (1):

$T_s = T_g - (Q*x)/(t*c*k*S)$, wherein c has the value of unity when all units are in the same system (ie., all CGS units).

From equation (1) it is a simple matter to derive the signal voltage output $V_s$ of the oxygen sensor using equation (2): $V_s = (T_s*R)/(4*F)*(Log((PO2_a)/(PO2_g)))$, wherein R is the gas constant, F is the Faraday constant, $PO2_a$ is the partial pressure of oxygen in the atmosphere, and $PO2_g$ is the partial pressure of oxygen in the exhaust gas.

According to the method of the present invention, equation (1) is rearranged to derive S using equation (3):

$S = (Q*x)/((T_g - T_s)(t*c*k))$.

Now, to determine the appropriate exposed surface area S of the sensor element tip, the known values for Q, x, $T_s$, $T_g$, t, c and k are input into equation 3, and the calculation is then performed.

One way to mechanically effect the appropriate exposed area S of the sensor element tip may be adjusted using the configuration of FIG. 3, wherein d is obtained by threading the threads more or less into the mounting member, and wherein $d = 2*S/(pi*x)$.

Another way to mechanically effect the appropriate exposed area S of the sensor element tip is to utilize a collar having a cavity for receiving therein the perforated cover. The collar is in good contact with the exhaust pipe, as for example by welding thereto. The exposed area of the sensor element tip may be adjusted any of three ways, in any combination: by adjusting d as measured with respect to the collar; by adjusting $A_1$, wherein $A_1$ is the concentric area of a gap between the sensor element tip and a cavity defining wall of the collar; and by adjusting $A_2$, wherein $A_2$ is the area of a hole formed laterally in the collar which communicates with the perforated cover (and $A_1$, if present) and has its axis parallel to the exhaust gas stream and faces directly thereinto; that is: $S = pi*x*d/2 + A_1 + A_2$, wherein the first term represents the surface area obstructive to the exhaust gas flow, and wherein the second term ($A_1$) may have less weight in defining S, even neglected, as ascertained empirically for a specific structural configuration.

Accordingly, it is an object of the present invention to provide a mechanical method for adjusting oxygen sensor placement in an exhaust pipe so that the oxygen sensor will operate below a predetermined maximum temperature.

This, and additional objects, advantages, features and benefits of the present invention will become apparent from the following specification.

BRIEF DESCRIPTION OF THE DRAWINGS

FIG. 1 is a diagrammatic representation of a prior art closed loop control system of gasoline internal combustion engine of a vehicle.

FIG. 2 is a side view of a prior art oxygen sensor.

FIG. 3 is a partly sectional view of the prior art oxygen sensor of FIG. 2 installed in an exhaust pipe of an internal combustion engine.

FIG. 4 is partly sectional view of the prior art oxygen sensor of FIG. 2 installed in an exhaust pipe of an internal combustion engine according to the structure and method of the present invention.

FIG. 5 is a top plan view of the prior art oxygen sensor as installed at FIG. 4.

FIG. 6 is a graph showing the effect of exposed surface area of the sensor element tip of an oxygen sensor on its output signal voltage.

DETAILED DESCRIPTION OF THE PREFERRED EMBODIMENTS

As recounted hereinabove, the method according to the present invention sets the exposed area of the sensor element tip (S), calculated from a formula which takes into account: the recommended maximum operational temperature of the oxygen sensor ($T_s$); the hottest expected temperature of the exhaust gas ($T_g$); the effective heat transfer rate from the exhaust gas to the sensor element tip, and ultimately to the surroundings, i.e., the exhaust pipe sidewall which is in contact with the surrounding ambient air (Q/t); the thermal conductivity of the oxygen sensor (k); and an effective thickness, which depends on where the temperature is measured in the oxygen sensor (x).

In that a manufacturer of an oxygen sensor will set a specific temperature range of operation for that model of oxygen sensor whereby ($T_s$) is set, in that the exhaust gas temperature can be measured for a specific vehicle undergoing operation that is strenuous to the engine whereby $T_g$ is determined, and in that the remaining variables k, t, x, and Q/t are all determinable, it is possible to predict an appropriate sensor element tip area exposure, as follows: $S=(Q*x)/((T_g-T_s)(t*c*k))$, wherein c is a conversion constant that ordinarily has the value of unity.

Now, to determine the appropriate exposed surface area S of the sensor element tip, the known values for Q, x, $T_s$, $T_g$, t, c and k are input into equation 3, and the calculation is then performed.

One way to mechanically effect the appropriate exposed area S of the sensor element tip may be adjusted using the configuration of FIG. 3, wherein d is obtained by threading the threads 30 more or less into the mounting member 32, and wherein $d=2*S/(pi*x)$.

Another way to mechanically effect the desired exposed area S of the sensor element tip is shown at FIGS. 4 and 5. A collar 50 has a cavity 52 which receives therein the perforated cover 28. The collar 50 is in good contact with the exhaust pipe 12, as for example by being a single piece with the mounting member 32' and the mounting member is welded 34 to the exhaust pipe, or by the collar being a separate piece welded directly to the exhaust pipe. The exposed area of the sensor element tip 24 may be adjusted any of three ways, in any combination: by adjusting d as measured with respect to the distal surface 54 of the collar 50; by adjusting $A_1$, wherein $A_1$ is the area of a gap 56 between the sensor element tip 24 and a cavity wall 58 of the collar; and by adjusting $A_2$, wherein $A_2$ is the area of a hole 60 formed laterally in the collar (ie., perpendicular to the cavity 52) which communicates with the perforated cover (and the gap 56, if present) and has its axis parallel to the exhaust gas stream and faces directly thereinto; that is: $S=pi*x*d/2+A_1+A_2$, wherein the first term represents the surface area obstructive to the exhaust gas flow, and wherein the second term ($A_1$) may have less weight in defining S, even neglected, as ascertained empirically for a specific structural configuration.

An example of carrying-out the above methodology will now be given.

$T_s$ was measured as 700 degrees C., the temperature of the exhaust gas, $T_g$, was measured as 850 degrees C., x was measured as 0.5 cm, k was estimated as 20 gm-cal/sec/cm$^2$/cm/Celsius degree, and S was measured as 0.47 cm$^2$; however, Q/t was not readily known. By using $S=(Q*x)/((T_g-T_s)(k))$, wherein c and t are set equal to one, Q/t was found to be 2825 gm-cal., wherein d=0.6 cm (assuming $A_1$ and $A_2$ are not used).

Now, using the method of the present invention, S was to be found for another $T_s$, specifically 556 degrees C., wherein the above value for Q/t (2825 gm-cal) was used in equation $S=(Q*x)/((T_g-T_s)(k))$. Upon performing the calculation, S was found to have a value of 0.24 cm$^2$, (d=0.3 cm). It was found from measurements, that the actual value of Q/t for this situation should have been set as 2300 gm-cal, in that the measured value of $T_s$ was 610 degrees C. However, the value of Q/t may be derived from a number of measurements, the tabulation of which would provide selective values of Q/t, which when used in the equation $S=(Q*x)/((T_g-T_s)(k))$ would provide higher accuracy. Nonetheless, the predicted value for S was close enough, in practice, for adjusting S satisfactorily within a recommended tolerance range.

FIG. 6 is a graph of the output signal voltage of an oxygen sensor, wherein it is empirically determined how the response characteristic of a sensor is altered by change in the exposed area of the sensor element tip. Plot A is the signal output voltage of an oxygen sensor having an area of 33 mm$^2$ in the exhaust gas stream, whereas Plot B is the signal output voltage of the oxygen sensor now having an area of 165 mm$^2$ in the exhaust gas stream. Plot A is sinusoidal, whereas Plot B is sinusoidal but includes noise, caused in part by the large surface area.

In the practice of the present invention, S is determined using the equation $S=(Q*x)/((T_g-T_s)(t*c*k))$, and S is mechanically adjusted according to $S=pi*x*d/2+A_1+A_2$, as discussed above. The value for S is then reviewed to determine if the operational characteristics will be sufficiently optimal (as per FIG. 6), before the mechanical adjustment is carried-out.

To those skilled in the art to which this invention appertains, the above described preferred embodiments may be subject to change or modification. Such change or modification can be carried out without departing from the scope of the invention, which is intended to be limited only by the scope of the appended claims.

What is claimed is:

1. A method for setting an appropriate exposed area of a sensor element tip of an oxygen sensor relative to an exhaust gas stream of an exhaust pipe, comprising the steps of:

determining a hottest recommended operating temperature ($T_s$) for the oxygen sensor;

determining a hottest expected exhaust temperature ($T_g$) of the exhaust gas;

determining an effective heat transfer rate (Q/t) from the exhaust gas to a sensor element tip of the oxygen sensor;

determining the thermal conductivity (k) of the oxygen sensor;

determining an effective thickness (x) of the oxygen sensor;

determining a desirable exposed surface area (S) of the sensor element tip in accordance with the determined values of ($T_s$), ($T_g$), (Q/t), (k) and (x) according to a relation $(S=(Q*x)/((T_g-T_s)(t*c*k)))$; and installing the oxygen sensor with respect to the exhaust pipe so that the exposed surface area of the sensor element tip thereof is substantially equal to (S).

2. The method of claim 1, wherein said step of determining (Q/t) is determined according to the relation $(S=(Q*x)/((T_g-T_s)(t*c*k)))$, wherein (S), (x), ($T_g$), ($T_s$), (t), (c) and (k) are known, and then using the determined value of (Q/t) to determine (S) for another value of ($T_s$).

3. The method of claim 1, wherein said step of installing comprises adjusting an outward extension distance (d) of the sensor element tip relative to a surface from which the sensor element tip projects into the exhaust stream, wherein (S) comprises at least in part an area defined by (d).

4. The method of claim 3, wherein said step of installing further comprises:

placing the sensor element tip into a cavity of a collar connected to the exhaust pipe, wherein the cavity is defined by a cavity wall of the collar; and setting a gap between the sensor element tip and the cavity wall; wherein (S) comprises at least in part an area defined by the gap.

5. The method of claim 3, wherein said step of installing further comprises:

placing the sensor element tip into a cavity of a collar connected to the exhaust pipe, wherein the cavity is defined by a cavity wall of the collar; and forming a lateral hole in the collar which communicates with the sensor element tip, wherein the hole has an axis oriented parallel to the exhaust gas stream and faces directly thereinto;

wherein (S) comprises at least in part an area defined by the hole.

6. The method of claim 3, wherein said step of installing further comprises:

placing the sensor element tip into a cavity of a collar connected to the exhaust pipe, wherein the cavity is defined by a cavity wall of the collar; and setting a gap between the sensor element tip and the cavity wall, wherein (S) comprises at least in part an area defined by the gap; and forming a lateral hole in the collar which communicates with the sensor element tip, wherein the hole has an axis oriented parallel to the exhaust gas stream and faces directly thereinto, and wherein (S) comprises at least in part an area defined by the hole.

7. The method of claim 1, wherein said step of installing comprises:

placing the sensor element tip into a cavity of a collar connected to the exhaust pipe, wherein the cavity is defined by a cavity wall of the collar; and setting a gap between the sensor element tip and the cavity wall; wherein (S) comprises at least in part an area defined by the gap.

8. The method of claim 1, wherein said step of installing comprises:

placing the sensor element tip into a cavity of a collar connected to the exhaust pipe, wherein the cavity is defined by a cavity wall of the collar; and forming a lateral hole in the collar which communicates with the sensor element tip, wherein the hole has an axis oriented parallel to the exhaust gas stream and faces directly thereinto;

wherein (S) comprises at least in part an area defined by the hole.

9. The method of claim 1, wherein said step of determining (Q/t) is determined according to the relation $(S=(Q*x)/((T_g-T_s)(t*c*k)))$, wherein (S), (x), ($T_g$), ($T_s$), (t), (c) and (k) are known, and then using the determined value of (Q/t) to determine (S) for another value of ($T_s$); and wherein said step of installing comprises at least one of:

adjusting an outward extension distance (d) of the sensor element tip relative to a surface from which the sensor element tip projects into the exhaust stream;

placing the sensor element tip into a cavity of a collar connected to the exhaust pipe, wherein the cavity is defined by a cavity wall of the collar, and setting a gap between the sensor element tip and the cavity wall, wherein the gap has an area ($A_1$); and forming a lateral hole in the collar which communicates with the sensor element tip, wherein the hole has an area ($A_2$), wherein the hole has an axis oriented parallel to the exhaust gas stream and faces directly thereinto;

wherein (S) is determined by any of (d), ($A_1$) and ($A_2$).

10. An apparatus for setting an exposure area of a sensor tip element of an oxygen sensor relative to an exhaust gas stream within an exhaust pipe, comprising:

an exhaust pipe; and a collar connected to the exhaust pipe, said collar having a cavity formed therein, wherein the cavity is oriented radially relative to the exhaust pipe, further comprising a hole laterally formed in said collar in perpendicular relation to said cavity, said hole communicating with said cavity, wherein said hole has an axis oriented parallel to the exhaust gas stream and faces directly thereinto.

11. The apparatus of claim 10, further comprising a sensor element tip of an oxygen sensor located at least in part in said cavity.

* * * * *